United States Patent [19]
DeVincenzo

[11] Patent Number: 5,938,437
[45] Date of Patent: Aug. 17, 1999

[54] BONY ANCHOR POSITIONER

[76] Inventor: John DeVincenzo, 1312 Garden St., San Luis Obispo, Calif. 93401

[21] Appl. No.: 09/054,208

[22] Filed: Apr. 2, 1998

[51] Int. Cl.⁶ .................................................... A61C 3/00
[52] U.S. Cl. ................................................. 433/18; 433/22
[58] Field of Search ................................. 433/17, 18, 20, 433/21, 22

[56] References Cited

U.S. PATENT DOCUMENTS

| | | | |
|---|---|---|---|
| 1,044,764 | 11/1912 | Federspiel | 433/18 |
| 3,691,635 | 9/1972 | Wallshein | 433/21 |
| 4,639,219 | 1/1987 | Gagin | 433/22 |
| 5,022,855 | 6/1991 | Jeckel | 433/18 |
| 5,035,614 | 7/1991 | Greenfield | 433/18 |
| 5,066,224 | 11/1991 | Block et al. | 433/18 |
| 5,697,779 | 12/1997 | Sachdeva et al. | 433/24 |

*Primary Examiner*—John J. Wilson
*Attorney, Agent, or Firm*—James B. Middleton

[57] ABSTRACT

A rigid buccally positioned bar, placed above the upper teeth and stabilized anteriorly by a connector to a protruding bony anchor carries a variety of force systems to facilitate tooth/teeth movement in all three spatial directions. The bar can be stabilized posteriorly by insertion into tubes on the molar bands. Various attachments connect different teeth to the buccally positioned bar for exerting the desired forces on the teeth.

3 Claims, 1 Drawing Sheet

BONY ANCHOR POSITIONER

BACKGROUND OF THE INVENTION

1. Field of the Invention

This invention relates generally to orthodontic treatment and appliances, and is more particularly concerned with a device that can be attached to a fixed subperiosteal or intra bony anchor, and from which pushing or pulling forces can be exerted to move teeth and correct malocclusions.

2. Discussion of the Prior Art

The use of fixed, immovable bony anchors as rigid objects from which to exert forces to move teeth has been considered in orthodontics for more than twenty years. See, for example, Sherman, A. J., "Bone reaction to orthodontic forces on vitreous carbon dental implants", *"American Journal of Orthodontics"*, vol. 74, p. 79, 1978, and Smith, J. R., "Bone dynamics associated with the controlled loading of bioglass-coated aluminum oxide endosteal implants," *American Journal of Orthodontics*, vol. 76, p. 618, 1979. These early studies used animal models, and it was not until 1983 that their use was demonstrated in clinical orthodontics. See Creekinore, T. A. and Eklund, M. K., "The possibility of skeletal anchorage", Journal of Clinical Orthodontics, vol. 17, p. 266, 1983. Thereafter, additional reports of the use of a bony anchor from which to exert forces to move teeth have appeared. See, for example, Turley, P, K., Gray, D. W., Kean, L. J. and Roberts, E. W., "Titanium endosseous and vitallium subperiosteal implants as orthodontic anchors for tooth movement in dogs", *Journal of Dental Research*, vol. 63A, p. 334, 1984, and Goodacre, C. J., "Rigid implant anchorage to close a mandibular first molar extraction site", *Journal of Clinical Orthodontics*, vol. 18, p. 693, 1994. More recently, interest has shifted to subperiosteal anchors as described by Block and Hoffman in U.S. Pat. Nos. 5,066,224 and 5,538,427, and in the article "A new device for absolute anchorage for orthodontics", *Journal of Orthodontics and Dentofacial Orthopedics*, vol. 107, p. 251, 1995.

All of the above mentioned anchor systems utilize either endoseous or subperiosteal placement and afford rigid, immovable objects from which forces can be exerted so teeth can be moved forward, backward, upward, downward, and sideways. All such anchors will be hereinafter referred to as bony anchors. However, the surgical placement of these anchors in numerous areas of the mouth is frequently very difficult because of limited access, or the presence of nearby roots, nerves, and blood vessels. Additionally, the means of attaching to these anchors is technically difficult, and complicated mechanical objects are required to facilitate tooth movement and orthodontic corrections. (an example see patent application of Devincenzo, application Ser. No. 08/948,731 filed Oct. 10, 1997.)

It is technically difficult to work in the back and roof of the mouth. It is easy to work in the front and along the sides of the mouth opposite the upper teeth.

SUMMARY OF INVENTION

This invention can be adapted to any of the previously mentioned bony anchors. Only a single bony anchor is needed, and this single anchor is placed in the front of the mouth and between the roots of the maxillary central incisors. Onto the anchor a connector is placed which stabilizes a rigid, heavy buccal wire shaped generally to match the dental arch. The ends of the buccal wire are attached into tubes on maxillary molar bands. Open or closed coil springs can be placed on this wire, or buccal arch, to move teeth forward or backward; the buccal arch can be expanded or constricted to move teeth sideways; and, elastic forces or open coil springs can be used to pull or push teeth up to, or down from, the buccal arch; so, the teeth can be moved in all three spatial directions.

This invention specifically addresses the use of the buccal arch positioner and the attachment mechanisms required to engage it to the bony anchor.

BRIEF DESCRIPTION OF THE DRAWINGS

These and other features and advantages of the present invention will become apparent from consideration of the following specification when taken in conjunction with the accompanying drawings in which.

DETAILED DESCRIPTION OF THE EMBODIMENT

Figure 1:
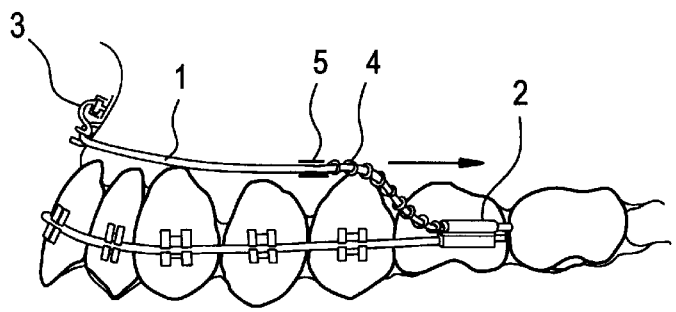
FIG. 1 is a side elevational view of a buccal arch made in accordance with the present invention, and showing its attachment to a bony anchor in the front of the mouth and being used in a way that will permit a force to be applied to the molar tooth to move it distally.

Referring now more particularly to the drawings, and to that embodiment of the invention here chosen by way of illustration, in FIG. 1 the buccal arch 1 is stabilized distally by insertion into the molar tube 2, while mesially it is held rigidly in place by the connector mechanism 3 which is fixed to a bony anchor. A length of open wound spring 4 is threaded over the buccal arch 1 from the distal end, and is prevented from moving mesially by stop 5 on the buccal arch. The spring 4 thus exerts a distalizing force on the molar.

Figure 2:
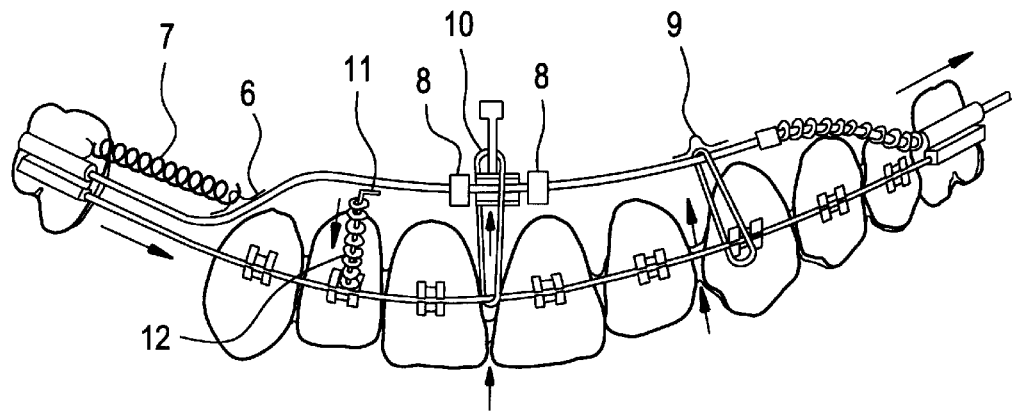
FIG. 2 is a frontal perspective view of the device shown in FIG. 1, showing the distalizing force of FIG. 1 on the left molar while a mesializing force is being applied to the right molar because of missing teeth, and intrusion forces are being applied to the central incisors and the left cuspid while an extensive force is present on the right lateral.

By modifying the shape of the buccal arch 1, as is well known by those in the practice of orthodontics, it can be used to exert a mesializing force on the molar as shown in FIG. 2. Herein an attachment 6 is placed on the buccal arch 1, and from the attachment 6 a force, such as that delivered by a closed coil spring 7, will produce the desired movement. Stops 8 on the buccal arch 1 will prevent migration of the buccal arch 1 from the forces applied through it. Tying directly to the buccal arch 1, or through an attachment 9 placed on it, will permit an intrusive force to be delivered to a tooth or teeth. A similar intrusive force is illustrated as being applied between the two centrals by way of an elastic thread 10. By attaching a vertical wire 11 from the buccal arch 1 extending towards the incisal (or occlusal) an open coil spring 12 could be placed on this vertical wire to extrude one or more teeth.

Figure 3:
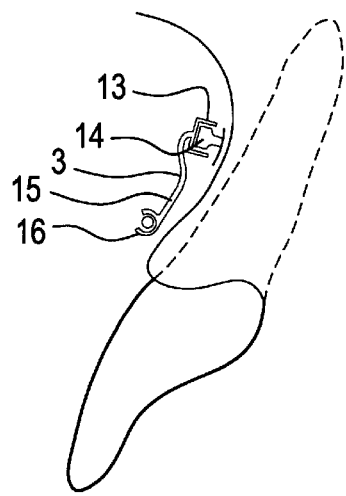
FIG. 3 is an enlarged side elevational view of the anchor shown in FIG. 1 showing the connector assembly more clearly; and, FIG. 4 is an enlarged front elevational view of the structure shown in FIG. 2.
Figure 4:
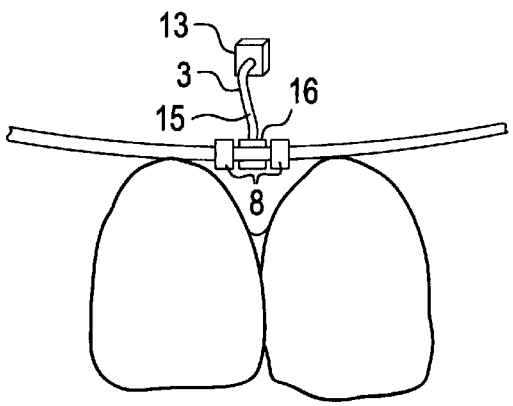

A connector mechanism 3 comprises three components (FIGS. 3 & 4). The angular cap 13 fits snugly over an angular shaft head 14 which protrudes from the body of the anchor. An adjustable connecting wire 15 extends from the cap to the angular U shaped receptacle 16 in which the buccal arch 1 rests. The wire 15 can be bent or otherwise adjusted to fit the individual patient. In the region of the receptacle, the buccal arch 1 may be angular (shown as round in FIG. 3) so it will fit more rigidly into the receptacle so as to create moments across the buccal arch to potentially intrude molars. To those familiar with the art of orthodontics, bending the buccal arch 1 apically in its posterior regions, i.e. giving it a curve of Spee, will effectively intrude those teeth, if the receptacle 16 and the buccal arch 1 in that region are both angular.

To those skilled in the art of orthodontics a further application of the buccal arch 1 to facilitate movement of the mandibular dentition will immediately come to mind. By using the buccal arch 1 as a stabilizing mechanism and not as an active tooth moving device, interarch forces can be delivered to the mandibular dentition. This would effectively serve as one or more mandibular bony anchors. Thus the mandibular dentition could be moved at will, utilizing forces generated from a single bony anchor provided at the midline of the maxillary central incisors.

While the details of the attachments and stops, such as attachment 9 and stop 8, are not shown, those skilled in the art are accustomed to fixing such apparatus to an arch wire or other appliance. The requirements for use of the present invention will therefore be well understood from the disclosure provided herein.

It will of course be understood by those skilled in the art that the particular embodiment of the invention here presented is by way of illustration only, and is meant to be in no way restrictive; thus, numerous changes and modifications may be made, and the full use of the equivalents resorted to, without departing from the spirit or scope of the invention as outlined in the appended claims.

What is claimed as invention is:

1. An orthodontic appliance for moving teeth in a desired direction, said appliance comprising, in combination, a single bony anchor for fixing in the oral cavity of a patient, an arch shaped wire fixed to said bony anchor shaped for extending buccally of the maxillary teeth and constituting a buccal arch, and resilient means for exerting forces between said buccal arch and at least one tooth of a patient, and further including at least one molar tube receiving an end of said buccal arch for stabilizing said buccal arch, wherein said bony anchor is to be fixed at the front of the oral cavity, said appliance further including a connector having a first end fixed to said bony anchor, and a second end fixed to said arch shaped wire.

2. An orthodontic appliance as claimed in claim 1 wherein said connector is adjustable to adapt to a given patient.

3. An orthodontic appliance as claimed in claim 1, and further including a pair of stops on said arch shaped wire, one stop of said pair of stops being at each side of said connector for stabilizing said wire with respect to said anchor.

* * * * *